United States Patent [19]

Webster

[11] 4,443,108

[45] Apr. 17, 1984

[54] OPTICAL ANALYZING INSTRUMENT WITH EQUAL WAVELENGTH INCREMENT INDEXING

[75] Inventor: Donald R. Webster, Laurel, Md.

[73] Assignee: Pacific Scientific Instruments Company, Anaheim, Calif.

[21] Appl. No.: 248,729

[22] Filed: Mar. 30, 1981

[51] Int. Cl.³ .............................................. G01J 3/50
[52] U.S. Cl. ............................ 356/418; 250/231 SE; 250/339; 350/315
[58] Field of Search ............... 356/332, 334, 308, 418, 356/419; 350/315, 318; 250/231 SE, 339

[56] References Cited

U.S. PATENT DOCUMENTS 3,385,160  5/1968  Dawson et al. ................. 356/328 X
4,082,464  4/1978  Johnson, Jr. .................... 350/315 X

FOREIGN PATENT DOCUMENTS

WO79/00464  7/1979  PCT Int'l Appl. ................. 356/418

OTHER PUBLICATIONS

Angus, UV Group Bulletin, No. 8, Part 1, Jun. 1980, pp. 53–60.

Angus, Optical Spectra, vol. 14, No. 8, Aug. 1980, pp. 49–52.

Primary Examiner—F. L. Evans
Attorney, Agent, or Firm—Lane, Aitken & Kananen

[57] ABSTRACT

In an instrument adapted particularly for analyzing agricultural products, such as grain, interference filters are rotated successively through an infrared wide wavelength band beam of light, which irradiates a sample of the product. Each of the interference filters operates to transmit a narrow wavelength band of light, the center frequency of which is scanned through a range of values as the angle of incidence of the beam of light to the interference filter varies as the filter rotates through the beam of light. An optical track is provided which rotates with the assembly of interference filters to generate pulses from index markings in the optical track. The markings in the optical track are spaced so that one pulse is generated for each angstrom of variation of the center frequency transmitted through an interference filter. The pulses are counted in the counter and the counts in the counter are used to control the selection of intensities reflected from the sample to be used in the analysis of the sample.

8 Claims, 2 Drawing Figures

OPTICAL ANALYZING INSTRUMENT WITH EQUAL WAVELENGTH INCREMENT INDEXING

BACKGROUND OF THE INVENTION

This invention relates to optical analyzing instruments and, more particularly, to optical analyzing instruments for testing samples from the reflective or transmissive properties of the samples.

In U.S. Pat. Nos. 3,861,788, issued Jan. 26, 1977 to Donald R. Webster; and 4,082,464 issued Apr. 4, 1978 to Robert L. Johnson, Jr., there are disclosed instruments for analyzing agricultural samples to determine the percentage of the constituents of the samples, for example, the protein, water and oil content of grain. In the instruments disclosed in these patents, the sample is irradiated with a narrow band wavelength beam of infrared light and the irradiating wavelength is scanned through a range of wavelengths. This is accomplished by an array of interference filters which are successively rotated through a wideband beam of infrared light and are tilted as they each move through the beam of light. This tilting of the interference filters causes the wavelength transmitted by the interference filter to be scanned through a range of wavelengths. At specific selected wavelengths, the intensity of the light reflected from or transmitted by the sample is detected and these intensities are used to determine the constituents in the sample. In the instruments disclosed in the patents, pulses are generated as the array of filters are rotated through the beam of light and are counted by a counter, which provides an indication of the angular position of the array of interference filters. Thus, the counts in the counter will correspond to specific wavelengths transmitted by the filters and irradiating to the sample. These counts are used to automatically select the wavelengths at which the reflected or transmitted intensities are detected and used in the sample analysis.

SUMMARY OF THE INVENTION

In accordance with the present invention, a circular track having pulse generating index marks is rotated in synchronism with the assembly of interference filters. A pulse generating means senses the marks in the track and generates pulses as the track is rotated to generate one pulse for each mark in the track. The marks are not evenly spaced in the track but are spaced in the track so that one pulse is generated for each angstrom of variation of the wavelength transmitted by an interference filter as such interference filter is moved and tilted through the light beam. As in the prior instruments, the pulses are counted by a counter, which is used to select the wavelengths from which the analysis of the sample is made. Because of the spacing of the index marks, each increment of count in the counter represents a one angstrom change in the wavelength transmitted by any given one of the interference filters. The fact that each increment of the counter represents a one angstrom change in the wavelength irradiating the sample simplifies the analysis of the sample and renders it more precise.

Further objects and advantages of the invention will become readily apparent from the following detailed description of the preferred embodiment of the invention when taken in conjunction with the accompanying drawings.

DESCRIPTION OF THE PREFERRED EMBODIMENT

Figure 1:
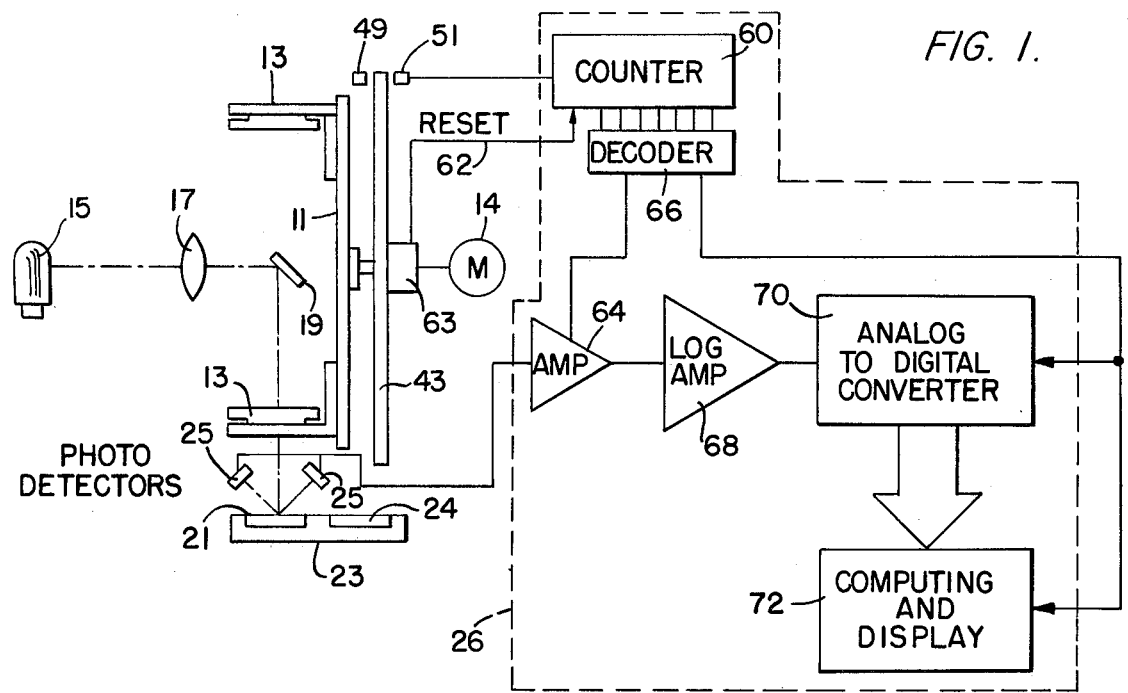
FIG. 1 schematically illustrates the instrument of the present invention.

As shown in the drawings, the analyzing instrument of the present invention comprises a turntable 11 on which six interference filters 13 are mounted, positioned in a cylindrical locus concentric with the axis of the turntable, with the interference filters equally distributed about the axis of the turntable. The turntable 11 is driven by a motor 14 to rotate the interference filters 13 continuously about the axis of the turntable 11. A wideband infrared light beam generated by a source 15 is collimated by a lens 17 and reflected by a mirror 19 into a beam passing through the cylindrical locus of the filters 13 onto a sample tray 23 containing an optical standard 24 and adapted to contain a grain sample 21. The tray 23 can be positioned to position the grain sample 21 to be irradiated by the beam from the source 15 or to have the optical standard 24 irradiated by the beam 24. The rotation of the turntable 11 brings the interference filters successively through the beam of light irradiating the sample 21 or the optical standard 24 and causing the angle of each interference filter to vary with respect to the light beam as the filter moves through the beam of light. Each interference filter 13 transmits a very narrow bandwidth and the center wavelength transmitted by each interference filter will vary with the angle of the interference filter to the incident beam. Thus, as each interference filter moves through the beam of light and varies its angular orientation with respect to the beam of light, the center wavelength of the narrow band transmitted through the interference filter will be scanned continuously through a range of wavelengths. Each of the six interference filters 13 is selected to scan through a different range of wavelengths preferably in the near infrared which is particularly useful when analyzing agricultural products such as grain. The narrow band of light irradiating the sample 21 or the optical standard 24 is reflected thereby and the reflected light is detected by photodetectors 25 which generate a signal indicative of the intensity of the reflected light. This signal is applied to an electronic analyzer system 26 which, from the applied signal, analyzes the sample and determines the percentage of constituents in the sample. For example, in the case of a grain sample, the analyzing system 26 determines the percentage amount of protein, oil and moisture content of the grain sample.

The grain sample 21 is contained in a removable sample holder so that measurements may be readily made on additional samples just by replacing one sample holder with a grain sample by another sample holder. Prior to making a measurement on a new grain sample, the tray 23 is positioned so that the optical standard 24 is irradiated and the signal representing the light intensity reflected from the optical standard 24, when applied to the optical analyzer 26, causes automatic calibration of the instrument.

The instrument as described to this point is substantially the same as that disclosed in U.S. Pat. No. 4,082,464, which is hereby incorporated by reference.

In the system disclosed in U.S. Pat. No. 4,082,464, pulses are generated as the turntable 11 is rotated to generate 1,000 pulses per revolution of the table 11 and these pulses are counted in the analyzer 26, which selects specific center wavelengths transmitted by the interference filters and the intensity of the reflected light at the selected wavelengths are used to analyze the sample. Because the pulses are generated at a rate of 1,000 per revolution, the analyzer 26 is operable to take measurements at 0.36 degree increments.

Figure 2:
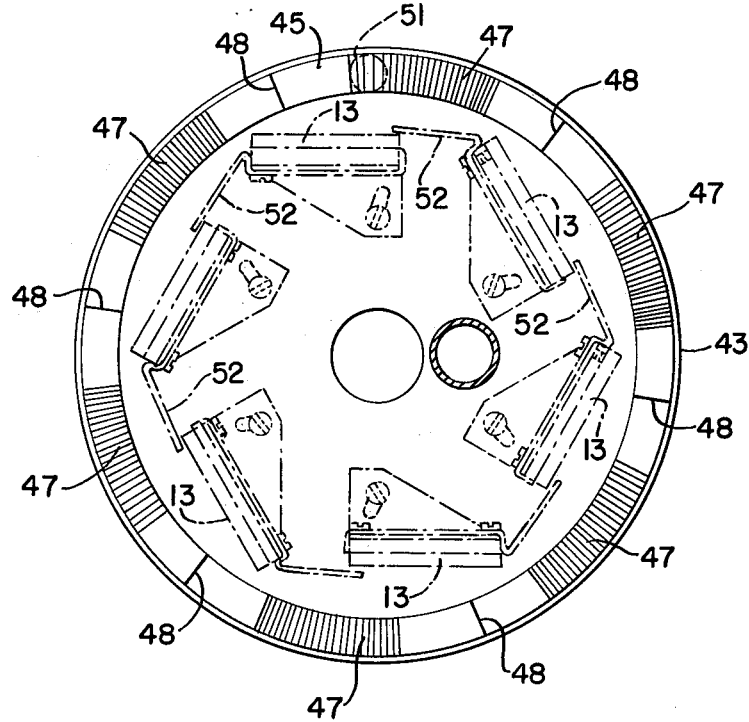
FIG. 2 schematically illustrates the optical track of the present invention and its relationship to the array of interference filters in the instrument of the invention.

In accordance with the present invention, instead of generating pulses at a rate of 1,000 per revolution, an optical index wheel 43 is used to generate pulses as the wheel is rotated. The wheel 43 is mounted on the same shaft by which the motor 14 drives the turntable 11 to rotate in synchronism with the turntable 11. As shown in FIG. 2, which is a plan view of the wheel 43 with the array of interference filters 13 shown superimposed in phantom on the wheel 43, the index wheel 43 is provided with a transparent circular track 45 concentric about the axis of the turntable 11. The track is provided with opaque radial index marks 47 and a light source 49 is arranged to shine a beam of light through the track 45 to be detected by a photocell 51. The photocell 51 is masked to have a linear radial transparent slit so that as each index mark in the track 45 comes opposite the photocell 51, it interrupts the light to the photocell 51 and causes the photocell 51 to generate a pulse. Alternatively, the track 45 could be opaque and the radial marks transparent.

In accordance with the present invention, the index marks 47 are spaced in the track 45 so that the light transmitted through each interference filter 13 will vary one angstrom for each pulse generated by the photocell 51. This greatly facilitates and simplifies the computations to be made by the analyzer 26 as is explained below. The fact that each pulse is generated for a one angstrom change in the wavelength being transmitted means that the index markings in the optical path cannot be equally spaced because the wavelength transmitted through an interference filter varies in accordance with the following function:

$$\lambda_\theta = \frac{\lambda_o(N - \sin^2\theta)^{\frac{1}{2}}}{N} \quad (1)$$

In this equation, $\theta$ is the angle of incidence, $\lambda_\theta$ is the center wavelength transmitted at an angle of incidence of $\theta \sim .\lambda_o$ is the center wavelength transmitted when $\theta$ is 0 or, in other words, when the interference filter is normal to the beam of light, and N is a constant, depending upon the index of refraction and other variables. Typically, N is equal to 1.45 for wavelengths below 2.22 micrometers and 1.95 for wavelengths above 2.22 micrometers. From the above equation, it will be apparent that the wavelength does not vary in equal increments with equal incremental changes of the angle of incidence, but varies more rapidly with changes in the angle as the angle of incidence increases. Accordingly, the index markings must be more widely spaced when the interference filter is nearer to normal to the beam of light and must be closer together for larger angles of incidence.

As shown in FIG. 2, the index markings 47 are arranged in six groups, one corresponding to each interference filter and each group of index markings will pass in front of the photocell as a given interference filter is passing through the beam of light over an angle of approximately 30°. In the spaces between each adjacent groups of index markings 47, a single isolated index mark 48 is provided. Each interference filter, as described in U.S. Pat. No. 4,082,468 has an opaque plate 52 which blocks the light from the sample between interference filters. While each of the opaque plates passes through the beam of light, one of the isolated index marks 48 will pass over the photocell 51 to generate a pulse for purposes to be explained below. As shown in FIG. 2, as the turntable 11 rotates clockwise, the filters will initially be brought into the beam of lignt at a maximum angle of incidence and as the interference filter rotates through the beam of light, the angle of incidence will be reduced toward zero angle of incidence as the beam approaches the other edge of the interference filter. Each group of index markings is positioned to begin passing in front of the photocell precisely at the time the full beam of light from the source is passing through an interference filter and the last index mark from the group passes in front of the photocell at the time that the leading edge of the beam of light reaches the opposite side of the photocell with the full beam of light still passing through the interference filter. The beam of light is rectangularly shaped with its long dimension perpendicular to the turntable 11 to increase the size of the angle through which the filter 13 tilts as it passes through the entire width of the beam of light as disclosed in copending application Ser. No. 236,543 entitled "RECTANGULAR IMPINGING BEAM" invented by the inventor of this application and filed Feb. 20, 1981. Since the interference filters enter the beam of light with a relatively high angle of incidence and tilt toward a zero angle of incidence as the filters move through the beam of light, the index markings are spaced so that they are closer together at the leading edge of each group which would first move across the photocell 51 as the disc 43 rotates clockwise as viewed in FIG. 2 and wider apart at the trailing edge of each group. The illustration of the markings in FIG. 2 is intended to be only representative of the variation and their spacing within each group as the actual markings will be much closer together than that illustrated.

The output pulses of the photocell 51 are applied to a counter 60 in the analyzer 26 which counts each pulse. Because of the way that the markings are spaced, each increment in the count of the counter 60 as one of the interference filters 13 is passing through the beam of light will represent a change in the wavelength transmitted of one angstrom. A reset pulse generated once per revolution on channel 62 by pulse generator 63 resets the counter 60 to zero, once per revolution. The reset pulses on channel 62 will be generated prior to the time that the next isolated index mark 48 passes the photocell 51 after one of the groups of index markings 47 has passed the photocell 51.

In a manner similar to that described in the Webster U.S. Pat. No. 3,861,788, the output signal of the photodetectors 25 is applied to a sensor amplifier 64, the details of which are disclosed in U.S. Pat. No. 3,861,788. As disclosed in this patent, the amplifier 64 has two functions: (1) to amplify the signal, and (2) to correct the output of the photodetectors 25 in accordance with the response of the photodetectors during the dark periods when no light is being transmitted to the sample tray in the spaces between the interference filters while the opaque plates 52 interrupt the beam of light. The sensor amplifier 64 measures and stores the output signal level of the photodetectors 25 during each dark period and subtracts this value from the output signal level of the photodetectors 51 during the next interval when the light beam is passing through an interference filter. In this manner, variation in the dark period response of the photodetectors is automatically compensated.

In order to cause the sensor amplifier 64 to store the output signal level of the photodetectors during the dark period, a decoder 66 responds to the counts in the counter 60 to signal the sensor amplifier 64. Because the counter 60 is reset to zero once per revolution, the counter 60 will have predetermined specific counts registered therein each time one of the isolated index marks 48 passes by the photocell 51 and causes it to generate a pulse to increment the counter 60. In response to these specific counts, the decoder 66 signals the sensor amplifier 64 to cause the sensor amplifier to store the output level of the photodetectors 25 during the dark periods between interference filters.

The output of the sensor amplifier 64 is amplified by logarithmic amplifier 68 which applies the amplified signal to an analog-to-digital converter 70. The decoder 66 responding to specific counts in the counter 60 actuates the analog-to-digital converter to convert the output signal level of the logarithmic amplifier 68 to digital signals and applies these digital signals to the computing and display unit 72. The counts in the counter 60, with the exception of those caused by the isolated index markings 48, will each represent a specific transmitted center wavelength irradiating the grain sample 21 or the optical standard 24 with each increment of count representing a variation in the transmitted center wavelength of one angstrom. The decoder 66 selects specific counts corresponding to those wavelengths to be used in the analysis to cause the analog-to-digital converter to convert the corresponding output signal of the logarithmic amplifier 68 to a digital value, which is then applied to the computing and display unit 72. The computing and display unit 72 stores the digital value for use in the analysis computation. The decoder 66 in addition to signaling the digital analog converter 60 to cause it to convert the output of the logarithmic amplifier 68 to a digital value at a specific transmitted center wavelength also signals the computing and display circuitry 72 to cause it to receive and store the applied digital representation.

Prior to making reflectance measurements on the sample, the sample tray 23 is positioned so that the optical standard 24 is irradiated with the light beam as the wavelength of the irradiating light is varied through its range of values by the rotation of the interference filters 13. While the sample tray is positioned so that the optical standard 24 is being irradiated, a signal is transmitted in response of this position on the sample tray to the display circuitry 72 to indicate that the digital data being received from the analog-to-digital converter 70 is from the optical standard. The wavelengths at which the logarithm of the intensity is detected and stored in the computing and display circuitry 72 as controlled by the decoder 66 in response to the counts in the counter 60 are the same as those for a grain sample measurement made on the grain sample 21. These values are stored as calibration values in the memory of the computing and display circuitry 72. Then, when the digital values are obtained from the grain sample 21, as described above, these calibration values are subtracted from the corresponding digital values obtained from the grain sample. This subtraction provides automatic compensation for drift in the signal level occurring in the amplifiers 64 and 68. The resulting difference values are the calibrated digital values which are used to analyze the sample.

The computation and display circuitry 72 determines percentage of protein, water and oil content of the grain sample in accordance with the following formulas:

$$P = k_{0p} + k_{1p}\frac{\Delta^2 OD_{mp}}{\Delta^2 OD_{rp}} \tag{2}$$

$$W = k_{0w} + k_{1w}\frac{\Delta^2 OD_{mw}}{\Delta^2 OD_{rw}} \tag{3}$$

$$O = k_{0o} + k_{1o}\frac{\Delta^2 OD_{mo}}{\Delta^2 OD_{ro}} \tag{4}$$

in which $k_{0p}$, $k_{1p}$, $k_{0w}$, $k_{1w}$, $k_{0o}$ and $k_{1o}$ are constants. The $E^2OD$ terms are approximations of a second derivative of a curve representing the variation in the reflective optical density with wavelength. The reflective optical density is a measurement of the ease in which the sample reflects light and is measured at a given wavelength by the logarithm of the ratio reflected intensity to the incident intentsity. Thus, reflective optical density at a given wavelength is expressed by $$OD = \log I_r/I_i \tag{5}$$

in which $I_r$ is the reflective intensity and $I_i$ is the incident intensity. The difference in the optical density at two closely spaced points will approximate the slope or first derivative of the optical density curve and is called $\Delta OD$. The difference in two $\Delta OD$ values taken at closely spaced points approximates the second derivative of the optical density curve and is called $\Delta^2 OD$. In equations (2), (3) and (4), above $\Delta^2 OD_{mp}$ is the value of $\Delta^2 OD$ centered about a wavelength selected to provide good correlation in equation (2) for the measurement of protein content; $\Delta^2 OD_{rp}$ is a reference value of $\Delta^2 OD$ centered about a wavelength at which the value of $\Delta^2 OD$ does not vary significantly with the protein content; $\Delta^2 OD_{mw}$ is the value of $\Delta^2 OD$ centered about a wavelength selected to have good correlation with the water content in the sample in equation (3); $\Delta^2 OD_{mr}$ is a reference value of $\Delta^2 OD$ centered about a wavelength at which the $\Delta^2 OD$ value does not vary significantly with the water content in the sample; $\Delta^2 OD_{mo}$ is the value for $\Delta^2 OD$ centered about a wavelength selected to correlate in equation (4) with oil content in the sample; and $\Delta^2 OD_{ro}$ is a reference value for $\Delta^2 OD$ centered about a wavelength at which the value of $\Delta^2 OD$ does not vary significantly with the amount of oil content in the sample. The value of $\Delta^2 OD$ centered about a given wavelength can be determined from the logarithm of the intensities of the reflected light at three closely spaced points, for example, three points A, B and C spaced 10 angstroms apart with wavelength A being 10 angstroms less than middle wavelength B and wavelength C being 10 angstroms greater than middle wavelength C, in accordance with the following equation:

$$\Delta^2 OD_B = \log I_C = 2\log I_B - \log I_A \tag{6}$$

in which $\Delta^2 OD$ is the value of $\Delta^2 OD$ centered about wavelength B, $I_C$ is the intensity of the reflected light at wavelength C, $I_B$ is the intensity of reflected light at wavelength B and $I_A$ is the intensity of reflected light at wavelength A.

Thus, it will now be apparent that the output values of the logarithmic amplifier 68 can be used to determine $\Delta^2OD$ values for any wavelength in the range caused to be scanned over the sample by the interference filters 13. To determine the value of $\Delta^2OD$ at wavelength B, the decoder 66 causes the analog-to-digital converter 70 to convert the output of the logarithmic amplifier 68 to digital at counts in the counter 60 corresponding to wavelengths A, B and C anc causes tne computing and display circuitry 72 to receive these digital values. The decoder 66 is set to provide logarithms of the reflected intensities to determine each of the $\Delta^2OD$ values for each of the equations (2), (3) and (4). The computing and display circuitry 72 after receiving these values corrects the received values in accordance with the response from the optical standard as described above by subtracting the previously stored calibration values from the received values, then determines rhe protein, water and oil content in accordance with equations (2), (3) and (4) from the corrected or calibrated values and provides a display of the results of the determination. It will be appreciated that because the index markings which generate the counts in the counter 60 are spaced exactly 1 angstrom apart in terms of the transmitted wavelength irradiating the sample, the selection of the points for determining $\Delta^2OD$ is considerably simplified. The decoder 66 simply enables the analog-to-digital converter and the computing and display circuitry 72 at 10 count intervals in the counter 60 and measurements are taken at precisely 10 angstrom intervals. The two wavelength intervals between the three measurement points are thus made exactly equal.

In the above described example, the sample 21 is a grain sample. It will be understood that the instrument can be used to analyze the constituents of other agricultural samples, industrial samples or other substances. In the instrument described above, the sample is analyzed by light reflected from the sample. Instead, the sample may be analyzed by light transmitted through the sample in which case the photodetectors would be positioned to receive light transmitted through the sample instead of reflected from the sample. In the case of light transmitted through the sample, the analysis may be made in a manner similar to that described above using tranmissive optical density instead of reflective optical density. Alternatively, the analysis may be made directly from the reflectance or transmittance of the sample instead of by the optical density of the sample. The sample, instead of being in a sample holder, may be fed into a chute and measurements made as the sample is transported past a measurement station, as disclosed in application Ser. No. 45,089 filed June 4, 1979 and invented by the inventor of this invention. The interference filters instead of being mounted in a drum arrangement as described in the above specific embodiment of the instrument may be arranged in a paddlewheel configuration like that disclosed in U.S. Pat. No. 3,861,788. Instead of using marks in an optical track to generate the pulses, other pulse generating indicia could be used. For example, the pulses could be generated by a transducer from magnetically recorded pulses in a magnetic track. In addition, the indicia could be spaced to provide other equal increments of wavelength change instead of 1 angstrom. These and many other modifications may be made to the above described invention without departing from the spirit and scope of the invention which is defined in the appended claims.

What is claimed is:

1. An optical analyzing instrument comprising means to generate a wide wavelength band beam of light, rotatable means including a filter and operating to rotate said filter through said beam of light continuously changing the angle of incidence of said filter to said beam of light as it rotates through said beam, said filter transmitting a narrow wavelength band of light and scanning the center frequency of the transmitted narrow wavelength band of light as the filter changes the angle of incidence with respect to said beam of light, means defining an annular track having linearly distributed marks in said track, transducer means having a sensing position to sense said marks passing through said sensing position and produce a pulse as each mark passes through said sensing position, means to impart relative rotation between said track and said transducer means in synchronism with the rotation of said filter to cause said marks to pass through said sensing position, said marks being unequally spaced in said track with the unequal spacing selected so that said transducer means generates one pulse for each equal increment of change of the center wavelength of the narrow wavelength band transmitted through said filter as said filter rotates through said beam of light.

2. An optical instrument as recited in claim 1, wherein there is provided means to count said pulses whereby each increment of count in said counter represents an incremental change in the center wavelength of the narrow wavelength band transmitted through said filter.

3. An optical instrument as recited in claim 2, wherein a sample is positioned to be irradiated by the light transmitted through said interference filter and means to detect the intensity of the light after the light transmitted through said interference filter comes into optical contact with said sample at predetermined counts in said counter.

4. An optical analyzing instrument as recited in claim 1, wherein said rotating means includes a plurality of filters and operates to rotate said filters in sequence through said beam of light continuously changing the angle of incidence of each filter as it rotates through said beam of light.

5. An optical instrument as recited in claim 4, wherein said rotating means rotates said filters about an axis, said filters being fixed relative to said axis and the rotational movement of said filters about said axis brings the filters in sequence into said beam of light.

6. An optical instrument as recited in claim 1, wherein said pulses are spaced relative to the rotation of said filters so that one pulse is generated for each angstrom of change in the center wavelength of the narrow wavelength band transmitted through said filter.

7. An optical instrument as recited in claim 1, wherein said annular track is fixed to said rotatable means to rotate at the same angular speed as said filter.

8. An optical instrument as recited in claim 4, wherein said marks comprise groups of unequally spaced marks in said track for each of said filters, each group rotating through the sensing position of said transducer means as the corresponding filter rotates through said beam of light, said groups of marks being spaced from each other in said track, and an index mark being defined in the space between each group of said marks in said track.

* * * * *